(12) United States Patent
Arango Cortes et al.

(10) Patent No.: US 12,011,322 B2
(45) Date of Patent: Jun. 18, 2024

(54) GUIDE AND SUPPORT FOR PERFORMING CRANIOFACIAL PUNCTIONS

(71) Applicant: FUNDACION ABOOD SHAIO EN REESTRUCTURACION, Bogota (CO)

(72) Inventors: Maria Lucia Arango Cortes, Bogota (CO); Carlos Javier Latorre Rojas, Bogota (CO); Fabian Cortes Munoz, Bogota (CO); Celso Ernesto Bohorquez Escobar, Bogota (CO); Jenny Carolina Sanchez Casas, Bogota (CO)

(73) Assignee: FUNDACION ABOOD SHAIO EN REESTRUCTURACION, Bogota (CO)

( * ) Notice: Subject to any disclaimer, the term of this patent is extended or adjusted under 35 U.S.C. 154(b) by 467 days.

(21) Appl. No.: 17/416,588

(22) PCT Filed: Apr. 24, 2019

(86) PCT No.: PCT/IB2019/053356
§ 371 (c)(1),
(2) Date: Jun. 21, 2021

(87) PCT Pub. No.: WO2020/217086
PCT Pub. Date: Oct. 29, 2020

(65) Prior Publication Data
US 2022/0054219 A1    Feb. 24, 2022

(51) Int. Cl.
*A61B 90/11* (2016.01)
*A61B 17/34* (2006.01)
(Continued)

(52) U.S. Cl.
CPC .............. *A61B 90/11* (2016.02); *A61B 17/34* (2013.01); *A61B 90/14* (2016.02); *A61B 2090/502* (2016.02)

(58) Field of Classification Search
CPC ......... A61B 90/11; A61B 90/14; A61B 90/50; A61B 2090/502; A61B 17/34;
(Continued)

(56) References Cited

U.S. PATENT DOCUMENTS

| 4,695,250 A | 9/1987 | Mariol |
| 8,414,597 B2 | 4/2013 | Kao et al. |

(Continued)

FOREIGN PATENT DOCUMENTS

| CN | 109091214 A | 12/2018 |
| CN | 109646124 A | 4/2019 |
| WO | 2013028811 A1 | 2/2013 |

*Primary Examiner* — Robert A Lynch
(74) *Attorney, Agent, or Firm* — Hoglund & Pamias, PSC; Roberto J. Rios

(57) ABSTRACT

The present invention is for use in the field of instruments and devices adapted for surgery and diagnostics with instruments. Specifically, it relates to a device for enabling the punction of particular anatomical structures in the craniofacial area. The device comprises a support frame in the form of an adjustable headband which may be adapted to the user's anatomy, a sphere with two arms that hold a placement fastener onto the face or cranium of the user, applying pressure to a specific position through the use of screws or rings that allow free movement on the hinges of the arms.

10 Claims, 9 Drawing Sheets

(51) Int. Cl.
*A61B 90/14* (2016.01)
*A61B 90/50* (2016.01)

(58) Field of Classification Search
CPC ............ A61B 17/3403; A61B 17/3423; A61B 2017/3405; A61B 2017/3407; A61B 2017/3409; A61B 2017/347; F16M 13/00; F16M 13/04; F16M 11/02; F16M 11/14
See application file for complete search history.

(56) References Cited

U.S. PATENT DOCUMENTS

| | | |
|---|---|---|
| 9,901,400 B2 | 2/2018 | Gowda et al. |
| 2010/0298846 A1 | 11/2010 | Kao et al. |
| 2017/0296295 A1 | 10/2017 | Wagner et al. |

GUIDE AND SUPPORT FOR PERFORMING CRANIOFACIAL PUNCTIONS

TECHNOLOGY SECTOR

The present invention can be used in the field of instruments and devices suitable for surgery and diagnostics. Specifically, it relates to a device used for enabling the punction of particular anatomical structures of the craniofacial area. The device comprises a support frame in the form of an adjustable headband that may be adapted to the user's anatomy, a sphere with two arms that hold the placement fastener onto the face or cranium of the user, applying pressure to a specific position through the use of screws or rings that allow free movement on the hinges of the arms.

STATE OF THE ART

Punction devices in various areas pose a challenge for the healthcare professional, owing to the ongoing risk of damaging adjacent structures during the procedure, since it is manually performed and the success depends on the user's skill. The use of devices entails factors such as difficulty in locating the exact point of punction and stability, orientation, and precision of the needle during the procedure. Likewise, existing devices are not equipped with mechanisms that allow the needle to remain in position while the trajectory to locate the target structure is established.

Existing state-of-the-art devices include solutions for fixing and adapting during surgery and performing punctions with fixing mechanisms using screws, or solutions that do not allow a gradual approach. However, there are no known solutions that may be effectively and safely applied for the punction of facial structures without hurting the user, or that may be securely fixed to irregular areas of the face, or that allow graduating the work area, or that allow the degrees of leeway to be varied.

Patent claim U.S. Pat. No. 9,901,400B2 "DISPOSITIVOS DE ACCESO ESTEREOTÁCTICOS Y SUS MÉTODOS" (STEREOTACTIC ACCESS DEVICES AND METHODS) is known in the state-of-the-art application, which allows such regions of the body as the skull to be accessed. This precursor has a fitting that shows a screw (103) adjustment to fit the surface of the body without any other type of hold and with no other mechanism for attachment to the facial area. With features similar to those of the precursor, it is not possible to perform facial punctions due to the fact that the facial section has irregular surfaces and the precursor cannot be tightly fitted to establish needle or cannula access without damaging the facial section. Furthermore, there is limited leeway available to the user in terms of mobility of the access device because this depends on the depth of insertion of the screws (103). The invention does not have a screw fitting method that may harm the user because inserting screws into the face is not viable when it comes to facial punctions. The invention proposes a novel solution for device fitting for craniofacial functions, unlike solutions known to the state of the art, without requiring the insertion of screws and tight fitting to irregular sections; the precursor does not have these features.

Patent U.S. Pat. No. 8,414,597 B2 "APARATO PARA APOYAR A AJUSTE QUIRÚORGICO" (APPARATUS FOR SUPPORTING SURGICAL ADJUSTMENT) comprises a support that allows for greater precision in procedures performed on different parts of the body. This precursor is equipped with various modes of use; however, all these have in common the fact that they adhere or attach to the surface of interest (150), primarily the cranium, through screws or other mechanisms that allow them to be correctly connected. Nevertheless, with this system it is challenging to achieve the support of the device on the face without using mechanisms that on the one hand, do not significantly harm the person, while on the other, manage to fix the support correctly onto the face for safely accessing the area of interest. Although in the patent for the precursor it is mentioned that the frame supports (342), (344), and (346) may be screws, bolts, coils, or other anchoring mechanisms to allow for the secure fixing of the subject's skull base, the base is circular and flat, and fixing it to the face, which is irregular, is not possible and cannot be achieved without screws. Precursor patent number U.S. Pat. No. 8,414,597 B2 may not be safely applied to facial punctions without leading to significant lesions on the face of the person or without imperceptible and forceful modifications to its design to enable it to be used.

Precursor US20100298846A1 "PLAFORMA QUIRURGICA UNIVERSAL" (ADJUSTABLE UNIVERSAL SURGICAL PLATFORM) is known, which is designed for use in the field of stereotactic neurosurgery, which implies that its design primarily applies to performing cranial punctions, which require a very different approach than that of facial punctions. This precursor has a "surgical platform" that envisages a perforated sphere in its interior, through which a probe is passed, and which is surrounded by a set of rings that allow it to rotate 360° until an activator located on the outer ring is pressed. For the probe to securely pass through the sphere, the rings, which act as stabilizers, are connected to a number of assemblies, which form mechanical supports with fixators on the bottom that are fitted to the patient's head. The precursor does not enable the diameter of the rings to be changed, thus preventing the simultaneous adjustment of the punction angle and site. In case of the new invention, the new device is made adaptable by changing the ring diameter and is applied with punction within a variable working area, determined by the change in ring diameter, which also allows for different punction strategies with a greater degree of freedom. The new patent also allows for differently sized probes to be used, as the perforation of the sphere has a variable diameter, as well as the ability to locate the working area in the face through nozzles on the support arches. Both attach or affix to the face or cranium without perforating the skin and guaranteeing that the device is secured.

Known devices that are most similar to the proposed invention cannot be implemented for performing facial punctions due to their screw hold or attachment that lead to lesions of the face or cranium for them to be attached securely. The invention proposes a novel solution for performing craniofacial punctions that is unknown to the state of the art and is unlike known solutions for fitting craniofacial devices without screws and with versatile needle movement and a graduated working area, with adaptable fixed location to reach structures that require maneuvering on the part of the practitioner to be effectively and securely punctured.

DESCRIPTION OF THE INVENTION

The guide and support for performing craniofacial punctions is a device for the punction of different craniofacial structures, as well as a teaching and training aid for improving craniofacial punction technique. It may also be used in other types of facial procedures where an instrument must be held securely at a specific point.

In particular, the invention is a device that can be used for improving the performance of facial punctions through the use of a support that adapts to the anatomy of the user and adjusts so as to provide stability and precision to the healthcare professional when performing cranioencephalic punction procedures. This improvement is reflected in the reduced requirement for further intervention for the user, reduced recovery time, more effective outcomes and less time between interventions which will ultimately allow the healthcare professional to proceed under the concept of safe surgery, with fewer mistakes and without causing harm to the user.

This device provides support for performing punctions in different regions of the face and skull. It has an arch-shaped structure that fits over the head and enables adaptation to the patient's anatomy, and the additional supports allow the needle to be placed at different angles in the posterior, anterior, and lateral areas of the face. This allows for the safe puncturing of different structures, avoiding lesions to the proximal structures. As well as modifying the angle, the central ring where the needle is inserted provides freedom to adjust the point of punction after adapting the entire support mechanism.

The attached figures illustrate the scope of the following proposal for a guide and support for performing craniofacial punctions:

DETAILED DESCRIPTION OF THE INVENTION

The present invention is a device used for the punction of specific anatomical structures of the craniofacial area, comprising a headband (1) made up of one arch (1a) that is connected to another arch (1c) with an upper adjustable tie (1b) that allows the distance between one arch (1a) and the other arch (1c) to be modified to fit the user's anatomy.

Figure 1:
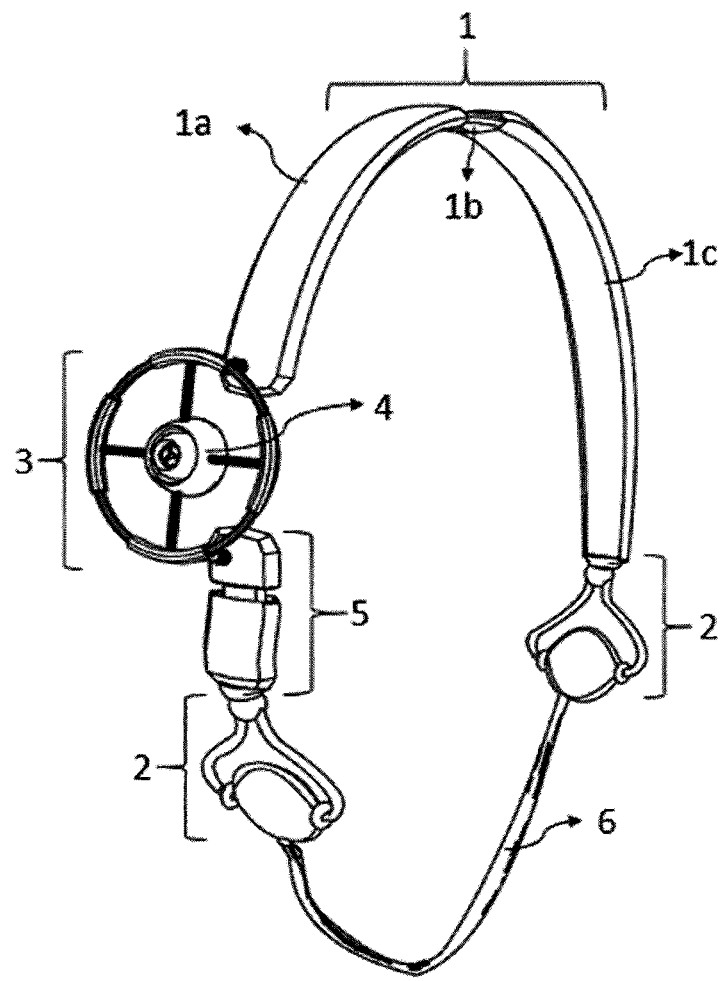
FIG. 1 shows a perspective view of the guide and support for performing craniofacial punctions
Figure 2:
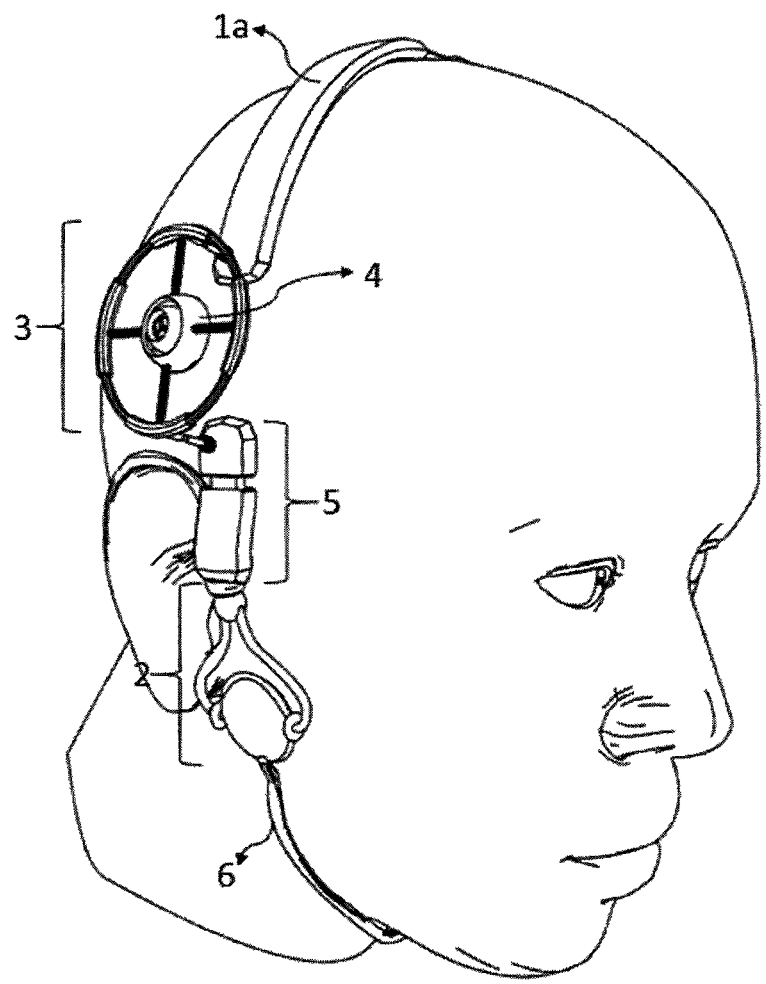
FIG. 2 shows an image of the fitting of the guide and support for performing craniofacial punctions on the user.
Figure 3:
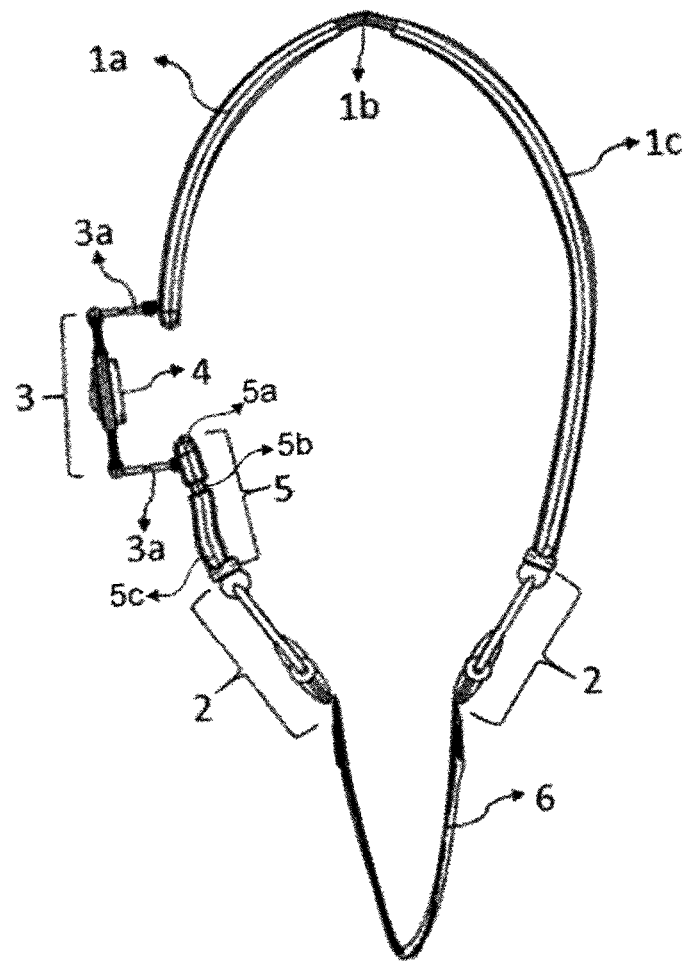
FIG. 3 shows a frontal view of the guide and support for performing craniofacial punctions with its main parts.
Figure 4:
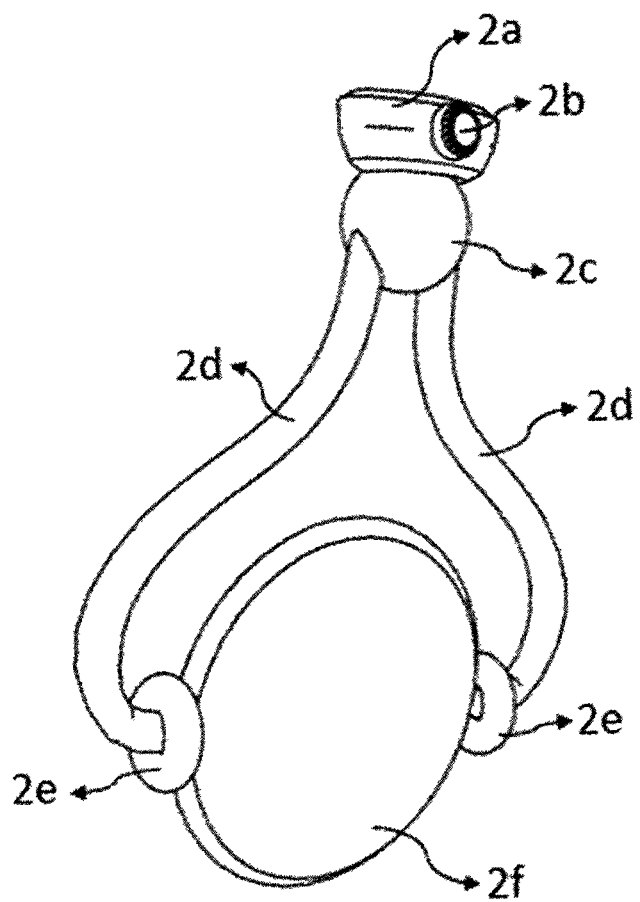
FIG. 4 shows an image of the fastening coupling that allows the headband to be fitted onto the cranium and face of the user.
Figure 5:
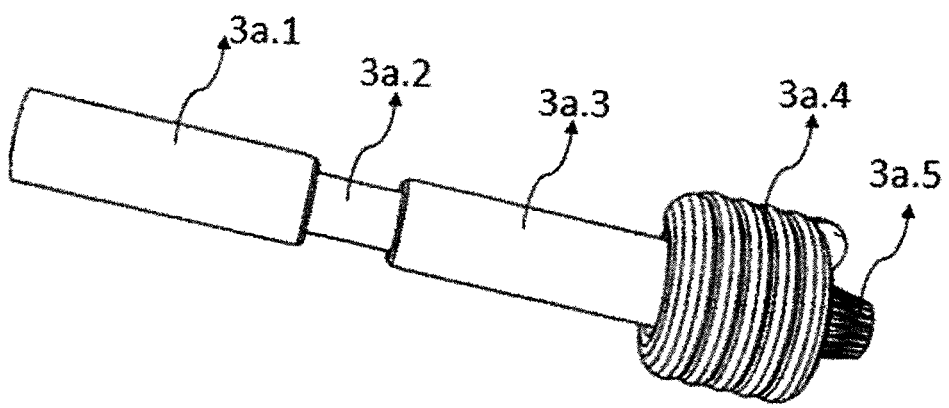
FIG. 5 shows an image of the adjustable base of the ring that supports the needle carrier.

A fastener coupling (2) is attached to the end of the arch (1c) in FIG. 4 to fix the headband (1) securely to the cranium, where a concave piece (2a) that connects to a spherical piece inside it (2c) is incorporated into this fastener coupling (2) to enable the spherical piece (2c) to be freely rotated. The mentioned spherical piece (2c) has a rod at one end, which is not shown, that locks with a clasp (2b) in the inner face of the concave piece (2a), whereby the mentioned clasp (2b), when pressed, secures the spherical piece (2c) in the desired position of the surface of the spherical piece (2c) on the interior of the concave piece (2a).

At the opposite end of the spherical piece (2c) there are two arms (2d) that hold the fastener (2f), which locates its surface over the face or over the cranium of the user by applying pressure to provide support. The fastener (2f) is affixed in a specific position with the slides (2e), and when they are not adjusted, they allow for the free movement of the fastener (2f) over the ends of the arms (2d), which act as a hinge for the fastener (2f).

At the end of the arch (1a) there is a ring with variable diameter (3) that connects to the end of the arch (1a) of the headband (1) with an adjustable base (3a) on one of its upper edges; on the lower edge the variable diameter ring (3) is connected to the lateral plate section (5) with an adjustable base (3a), where the adjustable bases (3a) of the edges allow the distance to be modified and apply pressure between the variable diameter ring (3) and the user.

The lateral plate section (5) comprises one lower plate (5c) and one upper plate (5a), which provide support and hold through an adjustable lateral tie (5b) that allows the distance between the lower plate (5c) and the upper plate (5a) to be modified.

The variable diameter ring (3) comprises a frame which, in different variations of the invention, may be circular, triangular, square, or polygonal, intended to be placed at key points of the cranium according to the anatomical structure on which the intervention is performed. The mentioned variable diameter ring (3) connects to a concentric needle carrier (4) through graduated hinges (3g), where the needle carrier (4) is composed of an outer rotating needle support (4a) and a central spherical support (4b) that rotates 360° inside the outer needle support (4a).

The adjustable base (3a) is composed of two hollow cylinders (3a.1) and (3a.3) connected by a rod (3a.2) that crosses them, allowing the length of the base to be adjusted and fixed in a particular position using the screw section (3a.4). Furthermore, there is a support (3a.5) that connects to the headband (1) and to the upper support (5a).

Figure 6:
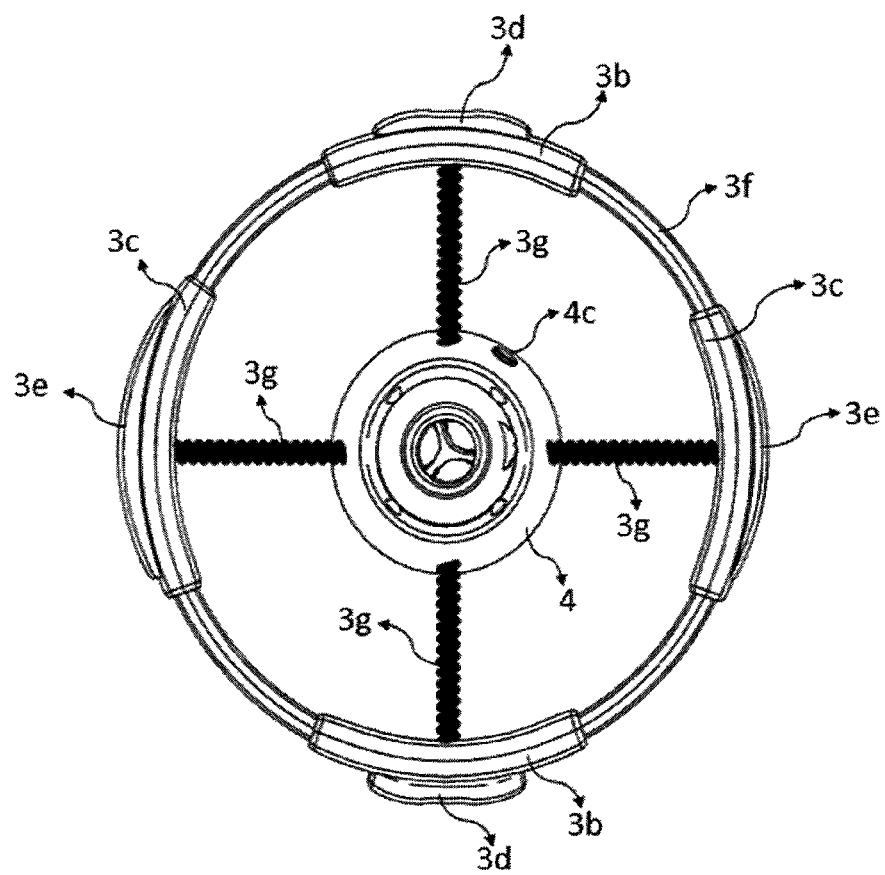
FIG. 6 shows a frontal view of the variable diameter ring that supports the needle carrier.

Each adjustable base (3a), in turn, is connected to several hollow cylinders (3b) where an elasticated ring passes (3f), followed by hollow cylinders (3c), which together form the variable diameter ring (3), as shown in FIG. 6, which allows the working area to be increased for the movement of the needle. Once the desired diameter of the working area is established inside the variable diameter ring (3), the hollow cylinders (3c) are secured by simultaneously pressing the opposing clasps (3e).

Each of the hollow cylinders (3c) has a hinge (3g) that connects the variable diameter ring (3) with the outer needle carrier (4a). These hinges (3g) are adjustable straps that enable the distance of the outer needle carrier and the variable diameter ring (3) to be increased.

The rotating outer needle carrier (4a) comprises a further external structure that is connected to the hinges (3g). This structure provides rigidity and stability to the rotating variable diameter ring (3) and may be moved in different directions within the variable diameter ring (3) by fixing the needle at a desired point by simultaneously pressing the opposing clasps (3d).

Figure 7:
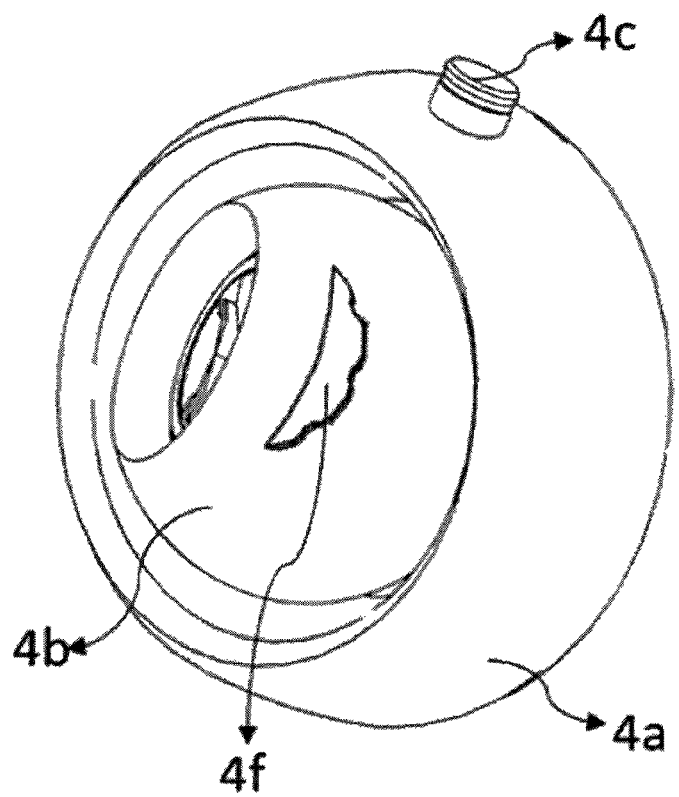
FIG. 7 shows an image of the needle carrier with the mechanism to secure the unsecured spherical central support.
Figure 8:
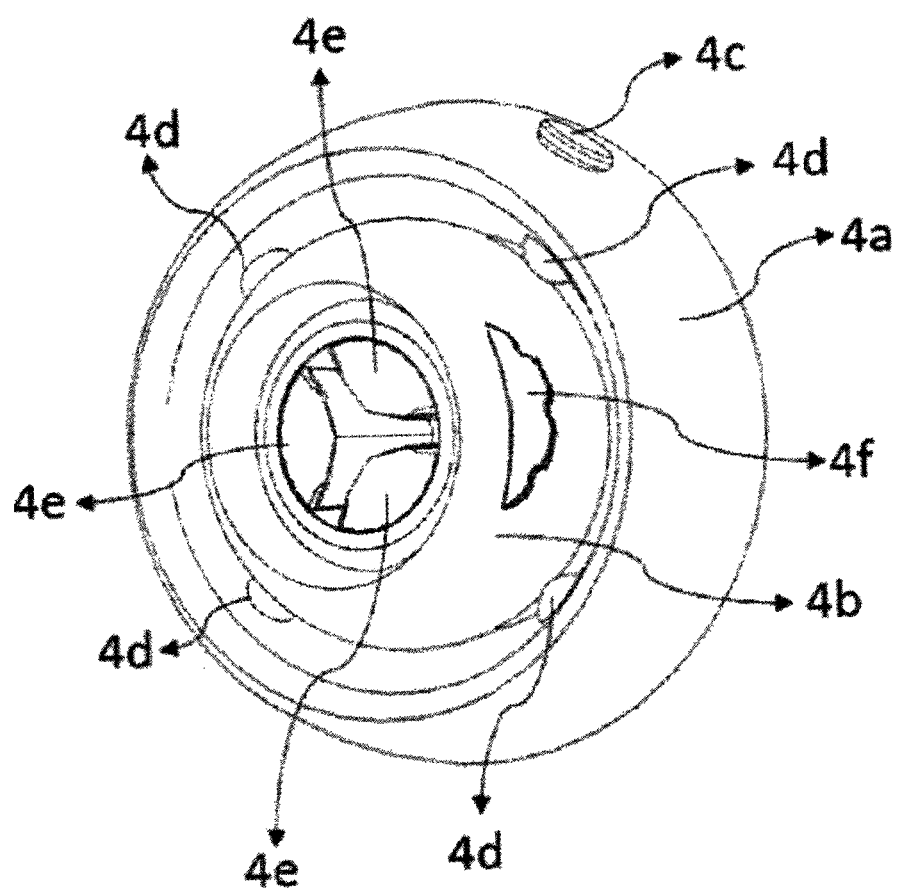
FIG. 8 shows an image of the needle carrier with the mechanism to secure the secured spherical central support.

FIGS. 7 and 8 show the spherical central support (4b) from different angles of its range of movement. This spherical central support (4b) is connected to an outer needle carrier (4a) and allows 360° internal rotation to vary the direction of the needle to perform the punction; it has a clasp (4c) that when pressed activates the wedges (4d) that immobilize the spherical central support (4b), securing it in a specific position.

The needle carrier (4) has three adjustable supports at the center (4e) that alter the central diameter through which the needle passes to adjust it to the size of the needle using a knob (4f) that when rotated gradually opens or closes the space of the supports (4e) that hold the needle.

Figure 9:
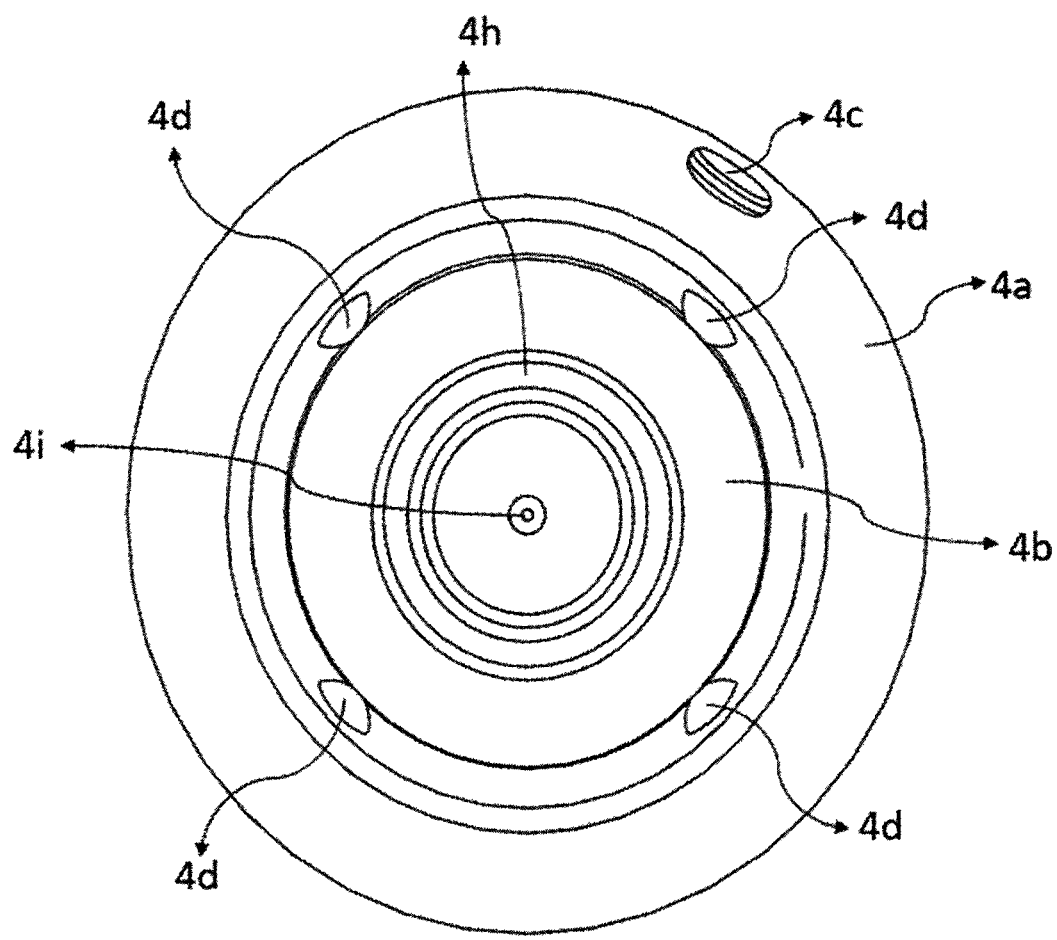
FIG. 9 shows an image of the alternate mechanism for fixation of the needle

FIG. 9 illustrates one modality of the invention with an alternate mechanism for fixing the needle with a tube (4h) filled with elastic material inside, which provides support and stability to the needle, but simultaneously allows it to slide through a small central channel (4i) that traps the needle, enabling punction.

Likewise, on the lower end of the lower plate (5c) there is the fastener coupling (2) where it connects the concave piece (2a) that connects to a spherical piece (2c).

The fastener (2f) connects to another opposing fastener (2f) through a detachable adjustable strap (6) to secure the headband (1) onto the user.

According to the figures detailed above, the external design presented in the figures does not constitute a limitation for the design of alternative forms of guide and support for performing craniofacial punctions, provided it does not conflict with the objective described herein.

The invention claimed is:

1. Guide and support for performing craniofacial punctions characterized by comprising:
    a variable diameter ring (3) that connects to a concentric needle carrier (4) through graduated hinges (3g), where an outer edge of said variable diameter ring (3) is connected to one arch (1a) of a headband (1) on one of upper edges of said variable diameter ring (3) and at a lower edge of said variable diameter ring (3) is connected to a lateral plate section (5), wherein the needle carrier (4) is composed of a rotating external needle support (4a) and a concentric spherical central support (4b) that rotates 360° inside the external needle support (4a); and
    a fastener coupling (2) composed of a concave piece (2a) that connects to a spherical piece (2c) for free rotation, where the spherical piece (2c) at one end has a rod that is held securely to an inner face of the concave piece (2a) with a clasp (2b), and at an opposite end, the spherical piece (2c) has two arms (2d) that hold a fastener (2f) whose surface is configured to apply pressure to a face or onto a cranium of a user, said fastener (2f) is fitted with slides (2e) and moves freely over ends of the arms (2d) and connects to another opposing fastener (2f) through a detachable adjustable strap (6) to secure the headband (1) to the user.

2. Guide and support for performing craniofacial punctions according to claim 1, CHARACTERIZED in that the arch (1a) of said headband (1) is connected to another arch (1c) with an upper adjustable tie (1b) that allows a distance between arch (1a) and arch (1c) to be modified to fit the user's anatomy.

3. Guide and support for performing craniofacial punctions according to claim 1, CHARACTERIZED in that the variable diameter ring (3) connects to one end of the arch (1a) of the headband (1) with an adjustable base (3a) on one upper edges of said variable diameter ring (3), and the lateral plate section (5) is connected to a lower edge of said variable diameter ring (3) with another adjustable base (3a), where the adjustable bases (3a) allow a distance to be modified and apply pressure between the variable diameter ring (3) and the user.

4. Guide and support for performing craniofacial punctions according to claim 1, CHARACTERIZED in that the lateral plate section (5) is formed from one lower plate (5c) and one upper plate (5a), connected with an adjustable side tie (5b) that established a distance between the lower plate (5c) and the upper plate (5a).

5. Guide and support for performing craniofacial punctions according to claim 1, CHARACTERIZED in that the variable diameter ring (3) has an adjustable base (3a) comprising two hollow cylinders connected by a rod (3a.2) which alters a length of the adjustable base and adjusts to a particular position through a screw section (3a.4), which connects to the headband (1) and to an upper support (5a) of the lateral plate section (5) with a support (3a.5).

6. Guide and support for performing craniofacial punctions according to claim 1, CHARACTERIZED in that the variable diameter ring (3) has adjustable bases (3a) which, in turn, are connected to hollow cylinders (3b), where a flexible ring (3f) passes, followed by hollow cylinders (3c) and has opposing clasps (3e) that establish a diameter of the working area.

7. Guide and support for performing craniofacial punctions according to claim 1, CHARACTERIZED in that the variable diameter ring (3) has opposing clasps (3d) that hold a needle.

8. Guide and support for performing craniofacial punctions according to claim 1, CHARACTERIZED in that the spherical central support (4b) has a clasp (4c) with wedges (4d) that immobilize the spherical central support (4b).

9. Guide and support for performing craniofacial punctions according to claim 1, CHARACTERIZED in that the needle carrier (4) has three adjustable supports inside (4e) with a knob (4f) that allows a space of the supports (4e) that hold a needle to be graduated.

10. Guide and support for performing craniofacial punctions according to claim 1, CHARACTERIZED in that the needle carrier (4) has a tube (4h) filled with elastic material and a central channel (4i) that holds a needle.

\* \* \* \* \*